United States Patent [19]
Takarada et al.

[11] Patent Number: 5,677,183
[45] Date of Patent: Oct. 14, 1997

[54] METHOD FOR CLASSIFYING AND COUNTING LEUKOCYTES

[75] Inventors: Kaoru Takarada; Chihiro Kouzuki; Yoshihiro Hyousa; Takashi Sakata; Yasumasa Akai, all of Hyogo, Japan

[73] Assignee: TOA Medical Electronics Co., Ltd., Hyogo, Japan

[21] Appl. No.: 464,056

[22] Filed: Jun. 5, 1995

[30] Foreign Application Priority Data

Aug. 3, 1994 [JP] Japan ................................. 6-182633

[51] Int. Cl.$^6$ ................................. G01N 31/00; G01N 33/48
[52] U.S. Cl. ................................. 436/10; 436/17; 436/63; 436/164; 436/166; 436/171; 436/175
[58] Field of Search ................................. 436/8, 10, 17, 436/18, 63, 164, 166, 171, 174, 175; 435/2

[56] References Cited

U.S. PATENT DOCUMENTS

| | | | |
|---|---|---|---|
| 4,933,293 | 6/1990 | Kuroda et al. | 436/63 |
| 5,116,539 | 5/1992 | Hanaguchi et al. | 436/10 X |
| 5,125,737 | 6/1992 | Rodriguez et al. | 356/39 |
| 5,242,832 | 9/1993 | Sakata | 436/17 |
| 5,250,437 | 10/1993 | Toda et al. | 436/10 |
| 5,389,549 | 2/1995 | Hanaguchi et al. | 436/10 |
| 5,496,734 | 3/1996 | Sakata | 436/63 |

OTHER PUBLICATIONS

JP 03020667 Abstract, WPIDS Accession. No. 91-070681, Jan. 29, 1991.

*Primary Examiner*—Jill Warden
*Assistant Examiner*—Maureen M. Wallenhorst

[57] ABSTRACT

A method for classifying and counting leukocytes which includes the steps of (i) adding a first reagent used for classifying leukocytes into four groups which contains, (a) at least one ionic surfactant in a sufficient amount to lyse erythrocytes and to damage a part of cell membrane of leukocytes, (b) at least one organic compound having an anionic group in a sufficient amount to bond with a cationic component present in leukocytes to give morphological differences between leukocytes, (c) a nonionic surfactant, and (d) a buffer for adjusting pH, to a part of a blood sample to determine information on the cell size and morphological features in order to classify leukocytes into four groups consisting of three groups corresponding to lymphocytes, mononuclear cells and eosinophils and one group corresponding to neutrophils and basophils; (ii) adding a second reagent used for measuring basophils to another part of the blood sample to determine information on at least the cell size in order to classify basophils, and (iii) classifying leukocytes based on the information obtained in the steps (i) and (ii) and counting.

23 Claims, 3 Drawing Sheets

Sensor of PD for receiving light

Photodiode (PD)

METHOD FOR CLASSIFYING AND COUNTING LEUKOCYTES

BACKGROUND OF THE INVENTION

1. Field of the Invention

The present invention relates to a method for classifying and counting leukocytes. In particular, it relates to a method for classifying leukocytes into five groups and counting each groups, by treating a blood sample with two kinds of reagents and measuring the treated blood sample.

2. Description of the Related Art

A number of devices and methods for classifying and counting leukocytes have been reported. According to such conventional devices, the blood is suitably treated with a lysing agent or staining solution and classified and counted based on physical and/or electrical characteristics or optical characteristics. It is also known that leukocytes can be classified and counted using a conventional flow cytometer.

As an example of a method for classifying and counting leukocytes, a method in which leukocytes are stained with fluorescent dye after lysing erythrocytes and the fluorescence is detected from the stained leukocytes is known. In addition, another method for classifying and counting leukocytes is also known in which basophils which are one of the subclasses of leukocytes are detected first, followed by determining other subclasses of leukocytes using another detecting system, whereby classifying leukocytes into five groups based on the respective data and counting.

The above mentioned conventional device which is available for classifying leukocytes into five groups and counting is expensive and the size thereof is large. Especially, when the conventional flow cytometer is used, the light source and photomultiplier tube (PMT) to be used are expensive. In addition, since an argon laser is employed for the light source, it is necessary to bear a maintenance fee and its optical axis should be always adjusted. Further, the device used for classifying leukocytes into five groups and counting needs two detecting systems, so that the device has a complicated structure.

According to a detecting device used for detecting two forward scattered lights having different angles in which beam spliter and pin holes are combined, the two angles of the scattered lights to be detected are limited depending on the shape of the pin holes.

SUMMARY OF THE INVENTION

The present invention provides a method for classifying and counting leukocytes comprising:

(i) adding a first reagent used for classifying leukocytes into four groups which comprises,
  (a) at least one ionic surfactant in a sufficient amount to lyse erythrocytes and to damage a part of cell membrane of leukocytes,
  (b) at least one organic compound having an anionic group in a sufficient amount to bond with a cationic component present in leukocytes to give morphological differences between leukocytes,
  (c) a nonionic surfactant, and
  (d) a buffer for adjusting pH,
to a part of a blood sample and measuring information on the size and morphological features, thereby classifying leukocytes into four groups consisting of three groups corresponding to lymphocytes, monocytes and eosinophils and one group corresponding to neutrophils and basophils and counting each groups;

(ii) adding a second reagent used for measuring basophils to another part of the blood sample and measuring information on at least the cell size, thereby classifying and counting basophils, and (iii) classifying leukocytes based on the information obtained in the steps (i) and (ii) into five groups and counting each groups.

The purpose of the present invention is to provide a method for classifying leukocytes into at least five groups and counting each groups by using an inexpensive device having a simple structure.

DETAILED DESCRIPTION OF THE INVENTION

Figure 1:
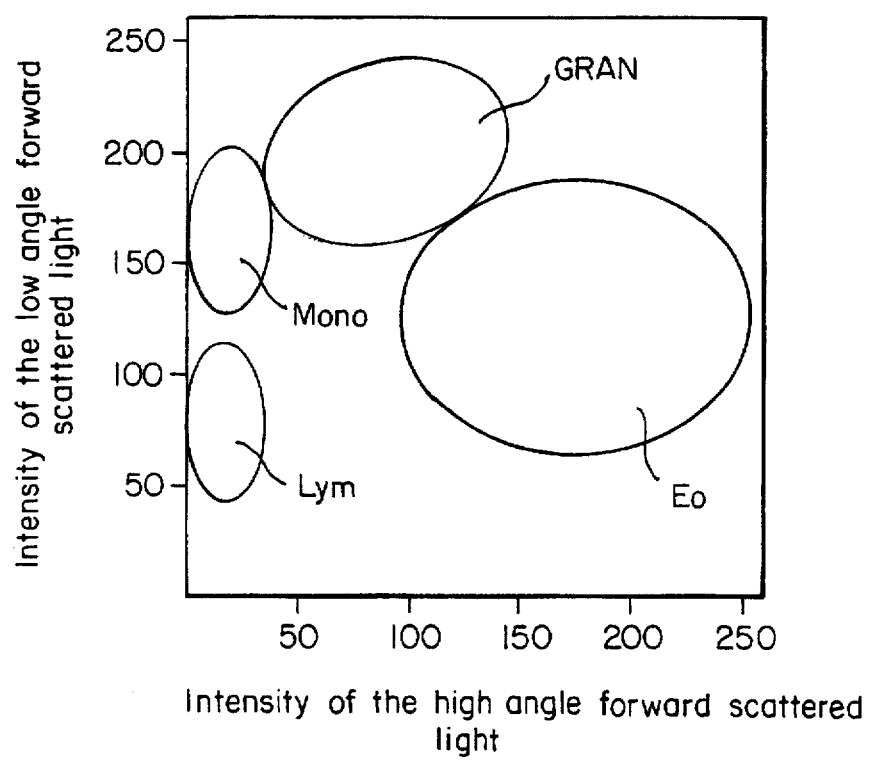
FIG. 1 is a scattergram showing the relationship between the intensity of the low angle scattered light and high angle scattered light when leukocytes are classified using the first reagent used for classifying leukocytes into four groups according to the method of the present invention (In FIG. 1, Lym means lymphocyte, GRAN means basophils and neutrophils, Mono means monocytes, Eo means eosionophils).

The present invention aims to classifying leukocytes at least into five groups and counting each groups. The blood sample used in the present invention includes a sample containing a whole blood or at least containing leukocytes.

The first reagent used for classifying leukocytes which is used in the step (i) of the method of the present invention comprises the ionic surfactant (a) in which at least one surfactant is selected from a cationic surfactant and an amphoteric surfactant. Preferred cationic surfactants are quaternary ammonium salt type or pyridinium salt type. The quaternary ammonium salt type and pyridinium salt type surfactants can be represented by the formula;

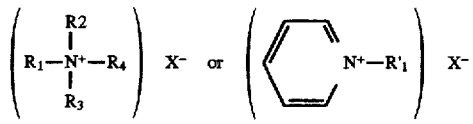

wherein $R_1$ or $R_1'$ is a $C_{6-18}$ alkyl or alkenyl group; $R_2$ and $R_3$ are a $C_{1-4}$ alkyl or alkenyl group; $R_4$ is a $C_{1-4}$ alkyl or alkenyl group, or benzyl group; and X is a halogen atom. The total number of carbon atoms in the above formula is preferably in the range from 9 to 30. Examples of the $C_{6-18}$ alkyl or alkenyl group for $R_1$ or $R_1'$ are hexyl, octyl, decyl, dodecyl or tetradecyl, hexenyl or heptenyl, preferably, a linear alkyl such as octyl, decyl or dodecyl. Examples of the $C_{1-4}$ alkyl or alkenyl groups for $R_2$ and $R_3$ are methyl, ethyl, propyl, butyl or butenyl, preferably, a $C_{1-3}$ alkyl such as methyl, ethyl or propyl. Examples of the $C_{1-4}$ alkyl and alkenyl groups for $R_4$ are methyl, ethyl, propyl, butyl or butenyl, preferably, a $C_{1-3}$ alkyl such as methyl, ethyl or propyl.

The amphoteric surfactants can be represented by the following formula;

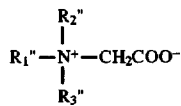

wherein $R_1''$, $R_2''$ and $R_3''$ are the same as $R_1$, $R_2$ and $R_3$ defined as above, respectively. The total number of carbon atoms in the above formula is preferably in the range from 9 to 30.

The above-mentioned ionic surfactant (a) is used in a sufficient amount to lyse erythrocytes and to cause damage to a part of cell membrane of leukocytes. Specifically, it is suitable to use about 30–5,000 mg/liter to the total volume of the first reagent, preferably about 50–3,000 mg/liter or, more preferably about 100–2,000 mg/liter, though it can be suitably modified depending upon the type of surfactant used or the like. Suitable concentrations for each of the ionic surfactants in the first reagent are given in Table 1. The ionic surfactant may be used singly or in a mixture of two or more surfactants.

TABLE 1

| Surfactant | Preferable concentration (mg/liter) |
| --- | --- |
| Octyltrimethylammonium bromide (OTAB) | 1000–5000 |
| Decyltrimethylammonium bromide (DTAB) | 200–3000 |
| Lauryltrimethylammonium chloride (LTAC) | 150–2000 |
| Myristyltrimethylammonium bromide (MTAB) | 100–1500 |
| Cetyltrimethylammonium chloride (CTAC) | 50–1000 |
| Stearyltrimethylammonium bromide | 50–500 |
| Cetyldimethylethtylammonium bromide | 50–500 |
| Laurylpyridinium chloride | 50–500 |
| Lauryldimethylaminoacetic acid betaine | 500–3000 |
| Stearyldimethylaminoacetic acid betaine | 500–3000 |

The ionic surfactant is required to possess a hemolytic activity of such an extent that makes pores in cell membrane of leukocytes through which an organic compound (discussed later) can pass but is not used in an amount that is potent to lyse the cell membrane so as to expose the cell nuclei. Accordingly, conventional cationic surfactants (e.g., LTAC, MTAB and CTAC) are usable but are used in far smaller amount than an amount for lysing the cell membrane so as to expose the cell nuclei and for inhibiting their own homolytic activities. Ionic surfactants possessing low hemolytic activity also are usable because it is sufficient to remove a part of membrane. The hemolytic activity of the ionic surfactant is in proportion to the carbon numbers of the hydrophobic group and, the more the carbon numbers, the more the hemolytic activity, therefore cationic surfactants having a low hemolytic activity such as DTAB and OTAB or amphoteric surfactant are preferably used.

In addition to the ionic surfactant, the first reagent used for classifying leukocytes into four groups contains the organic compound (b) having an anionic group which gives morphological differences among leukocytes by bonding with a cationic component present in leukocytes. Specifically, examples of the organic compounds include those having a hydrophobic group (such as an aromatic group, hydrocarbons having at least six carbon atoms and a heterocyclic ring having at least 6 carbon atoms) and an acidic group (anionic group such as carboxyl group and sulfonic acid group) and being negatively charged in an aqueous solution and capable of bonding with leukocytes to change the morphological features of leukocytes. The type of the organic compounds is not particularly limited and almost all kinds of acidic dyes can be used. Further, other organic compounds other than dyes are applicable as well because there is no need to measure the absorbency and the fluorescence intensity. Examples of the acidic dyes are Amido Black [Color Index No. 20470], Alizarin Cyanine Green F [CI No. 61570], Acid Green 27 [CI No. 61580], Acid Blue 62 [CI No. 62045], Direct Red 31 [CI No. 29100], Brilliant Sulphaflavine [CI No. 56205], Alizarin Yellow R [CI No. 14030], Acid Blue 129 [CI No. 62058], Acid Green 25 [CI No. 61570], Chromotrope 2R [CI No. 16570], Coomassie Brilliant Blue R-250 [CI No. 42660], Carmine Acid [CI No. 75470], Coomassie Brilliant Blue G-250 [CI No. 42655], Carmoisine B [CI No. 14720], Direct Blue 86 [CI No. 74180], Ethyl Red [2-(4-diethylaminophenylazo) benzoic acid], Para Rosaniline [CI No. 42500], Violamine R [CI No. 45190], Acid Yellow 34 [CI No. 18890], Acid Orange 51 [CI No. 26550], Brilliant Crocein MOO [CI No. 27290], Guinea Green B [CI No. 42085], Acid Blue 29 [CI No. 20460], Rhodamine B [CI No. 45170], Sulforhodamine B [CI No. 45100], Lissamine Green B [CI No. 44090], Acid Blue 9 [CI No. 42090], Fast Green FCF [CI No. 42053], Azocarmine B [CI No. 50090], Aniline Blue [CI No. 42780], Alphazurine A [CI No. 42080], Alizaline Violet 3R [CI No. 61710], Acid Blue 41 [CI No. 62130], Bieblich Scarlet [CI No. 26905], Erythrosin B [CI No. 45430], Methyl Red [CI No. 13020], Methyl Orange [CI No. 13025], Orange I [CI No. 14600], etc.

Examples of the organic compounds other than dyes are aromatic organic acids having hydrophobic and acidic functional group or acids having hydrocarbon of at least six carbon atoms or having heterocyclic ring. More specifically, their examples are 8-anilino-1-naphthalenesulfonic acid, 6-(p-toluidino)-2-naphthalenesulfonic acid, chromotropic acid, phthalic acid or naphthalenesulfonic acid or salts thereof. The amount of such organic compound may be suitably chosen depending upon the type of surfactant used or the like and is, preferably, about 50–5,000 mg/liter to the total volume of the first reagent or, more preferably about 100–3,000 mg/liter.

The first reagent used for classifying leukocytes into four groups further contains the nonionic surfactant (c). There is no particular limitation on the type of the nonionic surfactants and almost all kinds of nonionic surfactants which can be generally used as solubilizer may be used. The examples are nonionic surfactants having polyoxyethylene glycol (POE), polypropylene glycol (POP) or a block copolymer of polyoxyethylene glycol-polypropylene glycol (POE-POP) as a hydrophilic component. When only one kind of nonionic surfactant is used, leukocytes may be lysed as a side effect in addition to the desired lysis of an insoluble substance formed between the ionic surfactant and the above described organic compound or a cell-constituting component. In such a case, it is preferable to use a combination of two or more nonionic surfactants having different additional molar numbers of the hydrophilic group with each other. Alternatively, the combined use of nonionic surfactants having different structures of the lipophilic groups with each other can prevent the side effect. The amount of the nonionic surfactant required for dissolving the insoluble substance varies depending upon the type of ionic surfactant used or the like and is generally in the range of about 0.5–10 g/liter to the total volume of the first reagent, preferably about 1–8 g/liter.

The first reagent used for classifying leukocytes further contains the buffer (d) for adjusting pH. Usually, there is no particular limitation on the type of the buffers so far as it is used for keeping pH constant and any buffers having a pKa of "a desired pH±2.0" may be used. The specific examples of buffers are MES, TRIS, HEPES, succinic acid, phthalic acid and citric acid. In the present invention, it is preferable to adjust pH of the first reagent to about 5–11 whereby the amount used may be at about 5–100 mM to the first reagent.

Alcohols or metal salts may be further contained in the first reagent without particular limitation. Preferable alcohols are those which are easily available at a low cost in an industrial scale, such as alkanols (e.g. methyl alcohol and ethyl alcohol) and alcohols having an aromatic ring (e.g. phenethylalcohol and 2-phenoxyethanol). For example, methanol is used at a concentration preferably at about 5–20% to the entire amount of the first reagent. As a very rough yardstick, in accordance with the increasing of the number of carbon atoms which consist the alcohols by every one carbon atom, the preferable concentration thereof in the first reagent is halved. In particular, when 2-phenoxyethanol is used, it is preferable to use it at 0.05 to 1%. Preferred examples of the metal salts are alkali metal salts such as sodium chloride, potassium chloride and lithium chloride. Usually, it is not necessary to use the alkali metal salt but, in the case of the apparatus wherein the measurement is conducted using a signal of electric resistance as mentioned later, the alkali metal is needed to adjust the electroconductivity of the sample to the value which is suitable for the measurement. The preferred amount in such a case is in the extent that the electroconductivity of the solution is about 5–20 mS/cm.

The first reagent used for classifying leukocytes into four groups comprises the ionic surfactant (a), organic compound (b), nonionic surfactant (c) and buffer (d) in water or aqueous medium. The first reagent is preferably used 2 to 100 parts to 1 part of the blood sample (volume/volume).

The second reagent used for measuring basophils which is used in the step (ii) of the method of the present invention is preferably those comprising:

(1) at least one nonionic surfactant having an additional molar number of polyoxyethylene of 3 to 10, (2) at least one cationic surfactant, and (3) a buffer for adjusting pH to 2.5 to 4.0, but it is not specifically limited thereto.

As the nonionic surfactant (1) contained in the second reagent used for measuring basophils, those represented by the following formula may be used.

wherein $R_{1a}$ is a $C_8$–$C_{18}$ alkyl or alkenyl group, $R_{2a}$ is —O— or —($C_6H_4$)—O—, and n is an additional molar number of polyoxyethylene and is a real number of 3 to 10.

In the above formula, examples of the $C_8$–$C_{18}$ alkyl or alkenyl group include octyl, nonyl, decyl, undecyl, lauryl (dodecyl), tridecyl, myristyl (tetradecyl), pentadecyl, cetyl (hexadecyl), heptadecyl and stearyl (octadecyl), among which dodecyl is preferred.

Specific examples of the nonionic surfactant are polyoxyethylene (4.2) dodecylether (BL4.2, manufactured by NIKKO Chemicals Co.), polyoxyethylene (9) dodecyl ether (BL9, manufactured by NIKKO Chemicals Co.), polyoxyethylene (5) dodecyl ether (manufactured by NIKKO Chemicals Co.), polyoxyethylene (5.5) cetyl ether (manufactured by NIKKO Chemicals Co.), polyoxyethylene (7) cetyl ether (manufactured by NIKKO Chemicals Co.) and polyoxyethylene (7) oleyl ether (manufactured by NIKKO Chemicals Co.).

The nonionic surfactant may be used at a concentration of 300 mg/l to 20,000 mg/l in the second reagent, preferably at 500 mg/l to 10,000 mg/l. Specifically, polyoxyethylene (3–10) dodecyl ether may be used at 500 mg/l to 8,000 mg/l. If the concentration of the nonionic surfactant is too low, the nonionic surfactant can not lyse the cell membrane so as to expose the nuclei of granulocytes other than basophils, while if the concentration is too high, the nonionic surfactant prevents the cationic surfactant from lysing the cell membrane so as to expose the nuclei of granulocytes other than basophils. When using a nonionic surfactant other than the above mentioned nonionic surfactant, for example those having a large additional molar number of polyoxyethylene, granulocytes other than basophils can not make their nuclei naked completely. On the other hand, when the additional molar number of polyoxyethylene is too small, it would be difficult to use the reagent because it is hardly dissolved in water.

Next, the cationic surfactant (2) used for the second reagent includes at least one cationic surfactant selected from the group consisting of a quarternary ammonium salt having the following formula and pyridinium salt type surfactant:

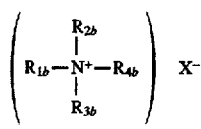

wherein $R_{1b}$ is a $C_{10}$–$C_{18}$ alkyl or alkenyl group, $R_{2b}$, $R_{3b}$ or $R_{4b}$ is a $C_1$–$C_3$ alkyl or alkenyl group and X is a halogen atom, or

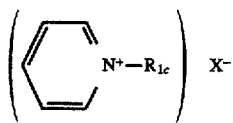

wherein $R_{1c}$ has the same meaning as $R_{1b}$ above, and X has the same meaning as above.

In the above formulae, examples of the $C_{10}$–$C_{18}$ alkyl or alkenyl group include decyl, undecyl, lauryl (dodecyl), tridecyl, myristyl (tetradecyl), pentadecyl, cetyl (hexadecyl), heptadecyl and stearyl (octadecyl), among which decyl, lauryl, myristyl, cetyl and stearyl are preferred.

Examples of the $C_1$–$C_3$ alkyl or alkenyl group include methyl, ethyl, propyl, ethynyl, propynyl and the like. Specific examples of cations are decyl trimethyl ammonium, lauryl trimethyl ammonium, myristyl trimethyl ammonium, cethyl trimethyl ammonium, cetyl dimethyl ethyl ammonium, lauryl dimethyl ethyl ammonium, myristyl dimethyl ammonium, lauryl pyridinium and cetyl pyridinium.

Examples of the halogen atom include fluorine, chlorine, bromine and iodine.

The above described cationic surfactants may be used at a concentration sufficient to nearly completely lyse erythrocytes and blood platelets and to expose the nuclei of at least granulocytes other than basophils. The preferable concentration is defined by observing the state of exposed nuclei with a general optical microscope. It ranges from about 100 mg/l to 10,000 mg/l to the total volume of the second reagent, preferably from 300 mg/l to 5,000 mg/l. The concentration is suitably adjusted depending on the type of the cationic surfactant. When the concentration is too low, erythrocytes and blood platelets are not sufficiently lysed, while the presence of excessive cationic surfactant facilitates exposing the nuclei of mononuclear cells.

Table 2 shows a preferable concentration and type of the cationic surfactants. These cationic surfactants may be used individually or in a mixture.

TABLE 2

| Surfactant | Preferable concentration |
| --- | --- |
| DTAB(decyl trimethyl ammonium bromide) | 1,000–10,000 mg/l |
| LTAC(lauryl trimethyl ammonium chloride) | 500–5,000 mg/l |
| MTAB(myristyl trimethyl ammonium bromide) | 400–4,000 mg/l |
| CTAC(cetyl trimethyl ammonium chloride) | 300–3,000 mg/l |
| STAC(stearyl trimethyl ammonium chloride) | 300–3,000 mg/l |
| CDMEB(cethyl dimethyl ethyl ammonium bromide) | 300–3,000 mg/l |
| CPyC(cetylpyridinium chloride) | 300–3,000 mg/l |

The cationic surfactants having the above mentioned formula are preferably used in the present invention. However, the type of cationic surfactant is not specifically limited thereto. Hemolytic activity of the cationic surfactant depends on the length of the main chain of its chemical structure. The longer the main chain is, the stronger the hemolytic activity is exhibited. Accordingly, the cationic surfactant having a long main chain can be used in a small amount.

The pH value of the reagent of the present invention is maintained by using the buffer (3) in the range from 2.5 to 4.0, preferably from 3.0 to 4.0. If the pH value is less than 2.5, the nuclei of immature granulocytes and monocytes are exposed. Accordingly, it would be difficult to classify leukocytes into each subclass. If the pH value is greater than 4.0, few leukocytes will be shrunk and their nuclei exposed, and few erythrocytes and blood platelets are hardly shrunk and hemolysed. The buffer used in the second reagent is not specifically limited and those having a pKa value in the range from 2.0 to 5.0 may be preferably used. The specific examples are citric acid, malic acid, diglycolic acid, succinic acid, formic acid and tartaric acid. The concentration of the buffer is not specifically limited. The buffer may be used at a concentration capable of adjusting a pH value to a desired range. Generally, 5 mM to 50 mM are preferably used.

The second reagent used for the present invention may be prepared by suitably selecting the above described nonionic surfactant (1), cationic surfactant (2) and buffer (3), and mixing them at a desired rate. Preferable examples of mixing are those comprising DTAB, BL4.2 and citric acid; LTAC, BL4.2 and citric acid; MTAB, BL4.2 and citric acid; CTAC, BL4.2 and citric acid; STAC, BL4.2 and citric acid; CDMEB, BL4.2 and citric acid; CPyC, BL4.2 and citric acid; DTAB, BL9 and citric acid; LTAC, BL9 and citric acid; MTAB, BL9 and citric acid; CTAC, BL9 and citric acid; STAC, BL9 and citric acid; CDMEB, BL9 and citric acid; CPyC, BL9 and citric acid; DTAB, BL4.2 and succinic acid; LTAC, BL4.2 and succinic acid; MTAB, BL4.2 and succinic acid; CTAC, BL4.2 and succinic acid; STAC, BL4.2 and succinic acid; CDMEB, BL4.2 and succinic acid; CPyC, BL4.2 and succinic acid; DTAB, BL9 and succinic acid; LTAC, BL9 and succinic acid; MTAB, BL9 and succinic acid; CTAC, BL9 and succinic acid; STAC, BL9 and succinic acid; CDMEB, BL9 and succinic acid; and CPyC, BL9 and succinic acid.

The second reagent used for the present invention may also contain metal salts. Generally, a salt is not necessary, however, if the sample has a low electric conductivity and is measured by detecting an electric impedance signal, the metal salts may be used to adjust the electric conductivity of the sample appropriately. The metal salts to be used is not specifically limited. For example, alkali metal salts such as sodium chloride, potassium chloride and lithium chloride are preferably used. Preferably, the alkali metal salts may be used in an amount to adjust the electric conductivity of the solution in the range from 3 to 20 mS/cm.

In order to classify and count leukocytes by using the second reagent of the present invention, a test sample used for measurement can be prepared simply by mixing the second reagent with the blood sample. When the second reagent and blood sample are mixed, each of the ingredients constituting the second reagent preferably comes in contact with the blood sample at the same time, but may be in contact with the blood sample sequentially depending on the type and concentration of the ingredients of the second reagent. The rate of the blood sample to the second reagent may be varied preferably by about 1:2 to 1:100, but it is not specifically limited to the rate. The action of the second reagent on the blood sample is very fast. The sample for measurement can be measured from about 10 seconds to 120 seconds without problems. The mixing temperature may be from about 10° C. to 40° C. When the temperature is high, the measurement must be carried out in a rather short period, while when the temperature is low, it must be carried out during a rather long period.

In addition to the second reagent described above, those having pH of 3.0 to 4.0 which comprises a nonionic surfactant having an additional molar number of polyoxyethylene of 12 to 30 and a cationic surfactant (see Japanese Laid-open Patent Publication Hei 3 (1991)-20667), and those having pH of 1.8 to 2.3 which comprises a diluted acid and a water soluble surfactant (see Japanese Laid-open Patent Publication Sho 61 (1986)-88896) may be used as the second reagent used for measuring basophils of the present invention.

The composition of the first reagent and the second reagent used for the present invention is not specifically limited to the composition described above. However, it is preferred that the blood sample treated with each of the reagents can be measured with the same measuring parameter. Further, in order to improve the reliability of counting, it is preferred that both of the reagents can be used by measuring at least the number of leukocytes.

A part of the blood sample to which the first reagent is added is subjected to measurement of the size and morphological features of the cells, thereby classifying leukocytes into four groups which consist of three groups corresponding to lymphocytes, monocytes and eosinophils and one group corresponding to neutrophils and basophils and counting each groups. In addition, another part of the blood sample to which the second reagent is added is subjected to measurement of at least the size of cells, thereby classifying and counting basophils. The methods used for measuring the size and morphological features of cells are not specifically limited. For example, a method for measuring both of the low angle scattered light and the high angle scattered light emitted by irradiating a light having a predetermined wavelength, or a method for measuring at least the low angle scattered light may be used. The low angle scattered light reflects the size of cells and the high angle scattered light reflects the morphological features of cells. As a measuring parameter which reflects the cell size, electric resistance can be used. The morphological features can be also reflected by measuring the side scattered light (90°). Preferred combination of the measuring parameters is made of the low angle scattered light and the high angle scattered light because the measurement can be conducted by a simple device shown in FIG. 3 when using the low angle scattered light and the high angle scattered light in combination. The blood sample treated with the second reagent may be measured after measuring the blood sample treated with the first reagent, or vice versa.

When mixing the blood sample with the first reagent used for classifying leukocytes into four groups, erythrocytes are lysed, whereby morphological features occur further between the subclasses of the leukocytes. As a result, leukocytes can be classified into four groups which consist of three groups corresponding to lymphocytes, monocytes and eosinophils and one group corresponding to neutrophils and basophils and counted.

On the other hand, when erythrocytes are lysed by mixing the blood sample with the second reagent used for measuring basophils, basophils remains almost as they are and other subclasses of leukocytes are shrunk. As a result, leukocytes can be classified into two groups consisting of basophils and other subclasses of leukocytes by measuring at least the low angle scattered light which reflects the cell size. It is preferable to measure both of the cell size and morphological features in case where the blood sample has a large number of leukocytes or immature granulocytes appear in the blood sample because not only the border line between basophils and other subclasses of leukocytes is made unclear but also left shift information is not obtained. More preferably, the second reagent used for measuring basophils comprises (1) at least one nonionic surfactant having an additional molar number of polyoxyethylene of 3 to 10, (2) at least one cationic surfactant, and (3) a buffer for adjusting pH to 2.5 to 4.0. When the second reagent described above is used, leukocytes can be classified into at least three groups consisting of basophils, mononuclear cells (including lymphocytes and monocytes) and granulocytes other than basophils, which means that immature granulocytes can be classified and counted.

Thus, leukocytes can be classified into five groups based on the information determined by treating leukocytes with the first reagent and the information determined by treating leukocytes with the second reagent. For example, the numbers of lymphocytes, monocytes and eosinophils are counted by using the first reagent, and the number of basophils is counted by using the second reagent. Then, the number of neutrophils can be counted by deducting the number of basophils from the total number of neutrophils and basophils. Alternatively, if the second reagent specifically described above is used, the number of neutrophils can be counted by deducting the number of eosinophils which is obtained by using the first reagent from the number of granulocytes other than basophils.

Figure 3:
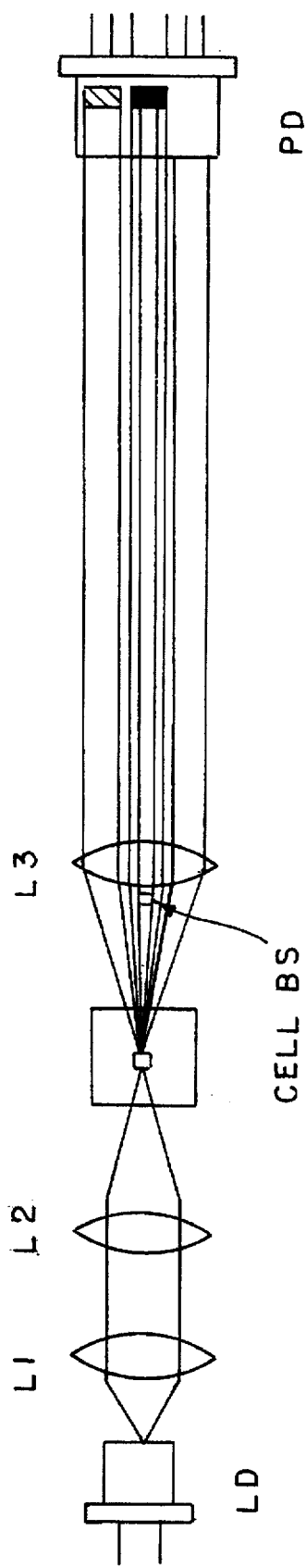
FIG. 3 shows a structure of a measuring device preferably used for the method of the present invention.

The blood sample treated with each of the first and the second reagent according to the present invention does not need to detect a fluorescent light, and can be determined by measuring a common measuring parameter. Accordingly, conventional devices for measuring leukocytes can be used. For example, it is preferred to use an inexpensive small analyzer provided with a semiconductor laser. When the analyzer is used, leukocytes can be classified and counted only by receiving two parameters comprising the forward low angle and high angle scattered lights. FIG. 3 shows an example of such a device provided with a semiconductor laser. A detector of the device comprises a semiconductor laser (LD) through a condenser lens (L2) and collimator lens (L1) in front of a flow cell (CELL) on a straight line, and a photodiode (PD) through a collector lens (L3) provided with a beam stopper (BS) behind the flow cell (CELL) on a straight line. The detector is characterized in that it comprises a semiconductor laser and is formed in a simple straight optical structure, and the two parameters comprising the forward low angle and high angle scattered lights can be distinguished by one photodiode (PD) itself.

Figure 4:
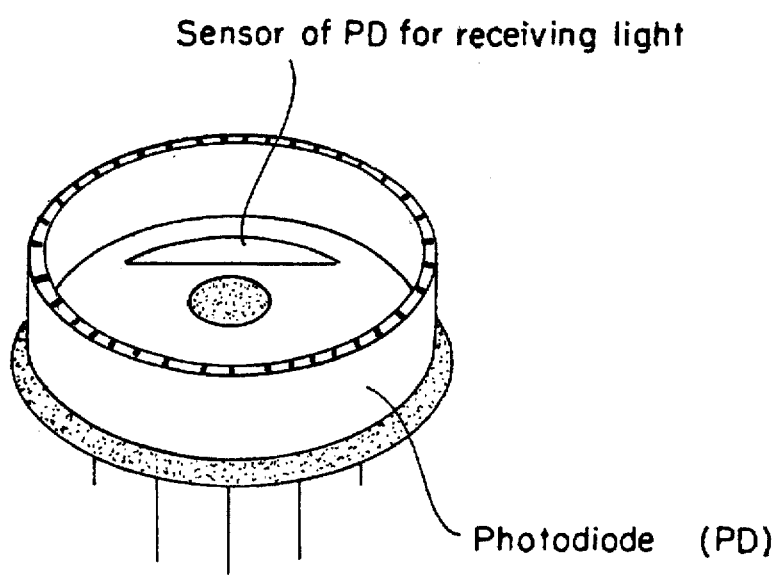
FIG. 4 is a perspective view showing a photodiode used for the measuring device of FIG. 3.
Figure 5:
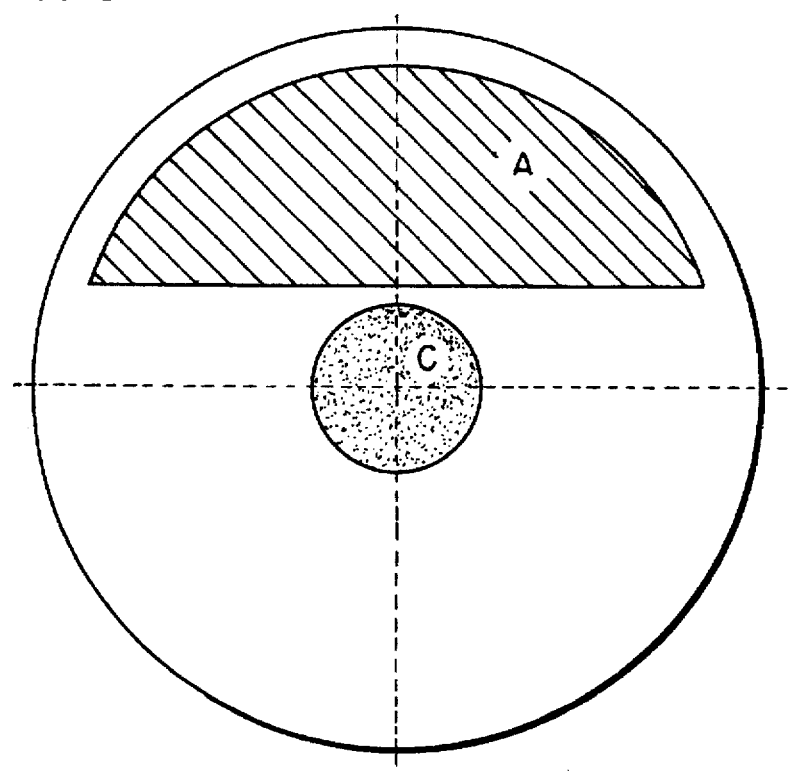
FIG. 5 is a schematic view showing a position of a sensor for receiving a light from the photodiode of FIG. 4.

FIG. 4 shows an example of the photodiode (PD) used in the device shown in FIG. 3. FIG. 4 is an outward appearance of the photodiode and FIG. 5 shows a position of a sensor of the photodiode to receive a light. The photodiode is housed in a tin type container similar to a general photodiode. A sensor C having a small circular shape located in the center detects the low angle forward scattered light (1° to 5°) and a sensor A having a semicircular shape on the upper side of the sensor C detects the high angle forward scattered light (6° to 20°), respectively. The sensitivity of the respective sensor is the same level as a general photodiode has. The separation of the sensor enables the device to measure the two signals of the scattered lights simultaneously.

The device used for the present invention is not specifically limited to the device described above, and conventional device or photodiode may be used.

The information on the cell size can be also obtained by measuring an electric resistance without measuring the low angle scattered light.

Example of the method for classifying and counting leukocytes of the present invention is described as follows.

EXAMPLE 1

A first reagent used for classifying leukocytes into four groups and counting each groups having the following formulation was prepared.

| (Composition of the first reagent) | |
| --- | --- |
| Decyl trimethyl ammonium bromide | 1.5 g/l |
| Magnesium 8-anilino-1-naphthalenesulphonate | 2.0 g/l |
| HCO-50 (nonionic surfactant, manufactured by NIKKO Chemicals Co.) | 4 g/l |
| PEN4630 (nonionic surfactant, manufactured by NIKKO Chemicals Co.) | 1 g/l |
| Phthalic acid | 50 mM |
| 2-Phenoxy ethanol | 2.5 ml/l |
| NaOH | in an amount to adjust pH to 5.5 |
| NaCl | 30 mM |

A second reagent used for measuring basophils having the following formulation was prepared.

| (Composition of the second reagent) | |
| --- | --- |
| Myristyl trimethyl ammonium bromide | 1 g/l |
| BL-9 (nonionic surfactant, manufactured by NIKKO Chemicals Co.) | 4 g/l |
| Citric acid | 10 mM |
| NaOH | in an amount to adjust pH to 3.3 |

Figure 2:
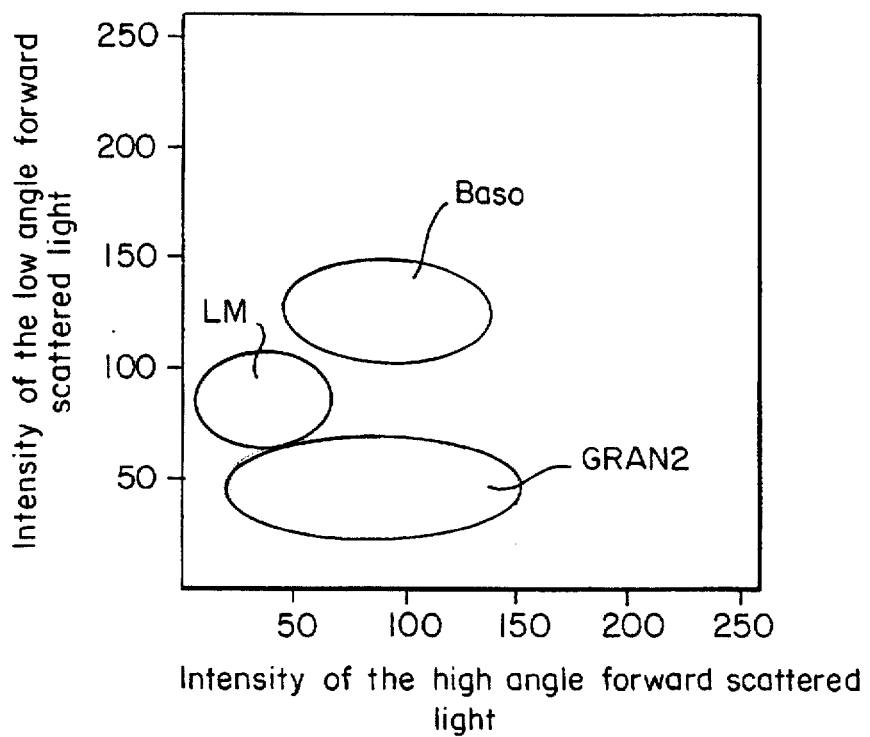
FIG. 2 is a scattergram showing the relationship between the intensity of the low angle scattered light and high angle scattered light when leukocytes are classified using the second reagent used for measuring basophils according to the method of the present invention (In FIG. 2, LM means lymphocyte and monocytes, Baso means neutrophils, GRAN2 means basophils and eosionophils).

The first reagent used for classifying leukocytes into four groups prepared as above (1 ml) was added to a blood sample (30 μl) taken from a normal subject. The intensity of the low angle forward scattered light and high angle forward scattered light were measured 10 seconds after mixing by a flow cytometer shown in FIG. 3. FIG. 1 and Table 3 show the results. Separately, the second reagent used for measuring basophils prepared as above (1 ml) was added to a blood sample (30 μl) taken from a normal subject. The intensity of the low angle forward scattered light and high angle forward scattered light were measured 30 seconds after mixing by a flow cytometer shown in FIG. 3. FIG. 2 and Table 3 show the results.

TABLE 3

| Number of leukocytes | First reagent used for classifying leukocytes into four groups 8014 | Second reagent used for measuring basophils 7917 |
|---|---|---|
| Lymphocytes | 19.2% | |
|  | 28.0% | 28.2% |
| Mononuclear cells | 8.8% | |
| Basophils | 68.8% | 0.7% |
|  | 72.0% | 71.8% |
| Neutrophils | | 71.1% |
| Eosionophils | 3.2% | |

As is clearly seen from FIG. 1, FIG. 2 and Table 3, the rates of lymphocytes and monocytes when using the first reagent and using the second reagent are coincident with each other, and the rates of basophils, neutrophils and eosinophils when using the first reagent and using the second reagent are also coincident with each other.

According to the method for classifying and counting leukocytes of the present invention, leukocytes can be classified into five groups and counted rapidly with an inexpensive system by using the first reagent used for classifying leukocytes into four groups and counting each groups, and the second reagent used for measuring basophils.

Moreover, since classification of leukocytes into four groups and of basophils are carried out two times by using the same detecting system, the reliability of counting can be improved by comparing the data such as the numbers of cells and their rate obtained by using the first reagent with the data obtained by using the second reagent. Namely, if the obtained data are different with each other, sort of warning can be given, thereby improving the ability of detecting abnormal cells.

What we claim is:

1. A method for classifying and counting leukocytes comprising:
   (i) adding a first reagent, used for classifying leukocytes into four groups, which comprises,
      (a) at least one ionic surfactant in a sufficient amount to lyse erythrocytes and to damage a part of cell membrane of leukocytes,
      (b) at least one organic compound having an anionic group in a sufficient amount to bond with a cationic component present in leukocytes to give morphological differences between leukocytes,
      (c) a nonionic surfactant, and
      (d) a buffer for adjusting pH,
   to an aliquot of a blood sample containing whole blood or containing at least leukocytes and measuring information on the size and morphological features of leukocytes, thereby classifying leukocytes into four groups consisting of three groups corresponding to lymphocytes, monocytes and eosinophils and one group corresponding to neutrophils and basophils and counting each group;
   (ii) adding a second reagent used for measuring basophils to an aliquot of said blood sample containing whole blood or containing at least leukocytes and measuring information on the size and on the morphological features of said basophils, thereby classifying and counting basophils from leukocytes other than basophils, and
   (iii) classifying leukocytes in said blood sample based on the information obtained in the steps (i) and (ii) into five groups and counting each group, wherein lymphocytes, monocytes and eosinophils are counted in step (i) and basophils are counted in step (ii), and neutrophils are counted by either deducting the number of basophils counted in step (ii) from the combined total of neutrophils and basophils counted in step (i), or by deducting the number of eosinophils counted in step (i) from the number of leukocytes other than basophils counted in step (ii).

2. The method for classifying and counting leukocytes according to claim 1, in which the information on the size of leukocytes is determined by irradiating light to the aliquot of the blood sample treated in step (i) or (ii) and measuring a low angle scattered light emitted thereby.

3. The method for classifying and counting leukocytes according to claim 2, in which an angle for measuring the low angle scattered light ranges from 1° to 5°.

4. The method for classifying and counting leukocytes according to claim 2, in which the information on the morphological features of basophils is determined by irradiating light to the aliquot of the blood sample treated in the step (ii) and measuring a high angle scattered light emitted thereby.

5. The method for classifying and counting leukocytes according to claim 1, in which the information on the size and morphological features of leukocytes is determined by irradiating light to the aliquot of the blood sample treated in step (i) and measuring low and high angle scattered light.

6. The method for classifying and counting leukocytes according to claim 1, in which the information in step (i) is determined by using a detector and the information obtained in the step (ii) is determined by using the same detector as in step (i).

7. A method for classifying and counting leukocytes comprising:
   (i) adding a first reagent, used for classifying leukocytes into four groups, which comprises,
      (a) at least one ionic surfactant in a sufficient amount to lyse erythrocytes and to damage a part of cell membrane of leukocytes,
      (b) at least one organic compound having an anionic group in a sufficient amount to bond with a cationic component present in leukocytes to give morphological differences between leukocytes,
      (c) a nonionic surfactant, and
      (d) a buffer for adjusting pH,
   to an aliquot of a blood sample containing whole blood or containing at least leukocytes and measuring information on the size and morphological features of leukocytes, thereby classifying leukocytes into four groups consisting of three groups corresponding to lymphocytes, monocytes and eosinophils and one group corresponding to neutrophils and basophils and counting each group;
   (ii) adding a second reagent used for measuring basophils to an aliquot of said blood sample containing whole blood or containing at least leukocytes and measuring information on the size and on the morphological features of said basophils, thereby classifying and counting basophils from leukocytes other than basophils, and
   (iii) classifying leukocytes in said blood sample based on the information obtained in the steps (i) and (ii) into five groups and counting each group, wherein lymphocytes, monocytes and eosinophils are counted in step (i) and basophils are counted in step (ii), and neutrophils are counted by either deducting the number of basophils counted in step (ii) from the combined total of neutrophils and basophils counted in step (i), or by deducting the number of eosinophils counted in step (i) from the number of leukocytes other than basophils counted in step (ii), wherein the information on the size of leukocytes is determined by irradiating light to the aliquot of the blood sample treated in step (i) or (ii) and measuring a low angle scattered light emitted thereby, and the information on the morphological features of basophils is determined by irradiating a light to the blood sample treated in step (ii) and measuring a high angle scattered light emitted thereby, said low angle scattered light reflects at least the size of leukocytes and the high angle scattered light reflects at least the morphological features of basophils.

8. The method for classifying and counting leukocytes according to claim 7, in which an angle for measuring the high angle scattered light ranges from 6° to 20°.

9. The method for classifying and counting leukocytes according to claim 7, wherein the at least one ionic surfactant is selected from the group consisting of a cationic surfactant and an amphoteric surfactant.

10. The method for classifying and counting leukocytes according to claim 9, wherein the cationic surfactant is a quaternary ammonium salt or pyridinium salt represented by the formulas:

$$\left[\begin{array}{c} R_2 \\ | \\ R_1-N^+-R_4 \\ | \\ R_3 \end{array}\right] X^- \text{ or } \left[\bigcirc\!\!\!\!\!\!-N^+-R'_1\right] X^-$$

wherein $R_1$ or $R'_1$ is a $C_{6-8}$ alkyl or alkenyl group; $R_2$ and $R_3$ are a $C_{1-4}$ alkyl or alkenyl group; $R_4$ is a $C_{1-4}$ alkyl or alkenyl group, or benzyl group; and X is a halogen atom.

11. The method for classifying and counting leukocytes according to claim 9, wherein the amphoteric surfactant is represented by the formula:

$$R_1''-N^+-CH_2COO^-$$
with $R_2''$ above and $R_3''$ below N wherein $R_1''$ is a $C_{6-18}$ alkyl or alkenyl group; and $R_2''$ and $R_3''$ are a $C_{1-4}$ alkyl or alkenyl group.

12. The method for classifying and counting leukocytes according to claim 7, wherein the at least one ionic surfactant is present in an amount of about 30–5,000 mg/liter based on the total volume of said first reagent.

13. The method for classifying and counting leukocytes according to claim 7, wherein the at least one organic compound is selected from the group consisting of an acidic dye, an aromatic organic acid having a hydrophobic and an acidic functional group, acids having a hydrocarbon of at least six carbon atoms, and acids having a heterocyclic ring.

14. The method for classifying and counting leukocytes according to claim 7, wherein the at least one organic compound is present in an amount of about 50–5,000 mg/liter based on the total volume of the first reagent.

15. The method for classifying and counting leukocytes according to claim 7, wherein the nonionic surfactant is present in an amount of about 0.5–10 g/liter based on the total volume of the first reagent.

16. The method for classifying and counting leukocytes according to claim 7, wherein the first reagent is present in an amount of 2 to 100 parts to 1 part of said aliquot of blood sample (volume/volume).

17. The method for classifying and counting leukocytes according to claim 7, wherein the second reagent comprises:

(1) at least one nonionic surfactant having an additional molar number of polyoxyethylene of 3 to 10, (2) at least one cationic surfactant, and (3) a buffer for adjusting pH to 2.5 to 4.0.

18. The method for classifying and counting leukocytes according to claim 17, wherein the at least one nonionic surfactant in the second reagent is represented by the following formula:

$$R_{1a}-R_{2a}-(CH_2CH_2O)_n-H$$

wherein $R_{1a}$ is a $C_8-C_{18}$ alkyl or alkenyl group, $R_{2a}$ is —O— or —($C_6H_4$)—O—, and n is an additional molar number of polyoxyethylene and is a real number of 3 to 10.

19. The method for classifying and counting leukocytes according to claim 17, wherein the at least one nonionic surfactant in the second reagent is present in an amount of 300 mg/l to 20,000 mg/l based on a total amount of the second reagent.

20. The method for classifying and counting leukocytes according to claim 17, wherein the at least one cationic surfactant for the second reagent comprises at least one cationic surfactant selected from the group consisting of a quaternary ammonium salt having the following formula:

$$\left[\begin{array}{c} R_{2b} \\ | \\ R_{1b}-N^+-R_{4b} \\ | \\ R_{3b} \end{array}\right] X^-$$

wherein $R_{1b}$ is a $C_{10}-C_{18}$ alkyl or alkenyl group, $R_{2b}$, $R_{3b}$ or $R_{4b}$ is a $C_1-C_3$ alkyl or alkenyl group and X is a halogen atom, and a pyridinium salt having the following formula:

$$\left[\bigcirc\!\!\!\!\!\!-N^+-R_{1c}\right] X^-$$

wherein $R_{1c}$ has the same meaning as $R_{1b}$ above, and X has the same meaning as X above.

21. A method for classifying and counting leukocytes comprising:

(i) adding a first reagent, used for classifying leukocytes into four groups, which comprises, (a) at least one ionic surfactant in a sufficient amount to lyse erythrocytes and to damage a part of cell membrane of leukocytes, (b) at least one organic compound having an anionic group in a sufficient amount to bond with a cationic component present in leukocytes to give morphological differences between leukocytes, (c) a nonionic surfactant, and (d) a buffer for adjusting pH, to an aliquot of a blood sample containing whole blood or containing at least leukocytes and measuring information on the size and morphological features of leukocytes, thereby classifying leukocytes into four groups consisting of three groups corresponding to lymphocytes, monocytes and eosinophils and one group corresponding to neutrophils and basophils and counting each group;

(ii) adding a second reagent used for measuring basophils to an aliquot of said blood sample containing whole blood or containing at least leukocytes and measuring information on the size and on the morphological features of said basophils, thereby classifying and counting basophils from leukocytes other than basophils, and (iii) classifying leukocytes in said blood sample based on the information obtained in the steps (i) and (ii) into five groups and counting each group, wherein lymphocytes, monocytes and eosinophils are counted in step (i) and basophils are counted in step (ii), and neutrophils are counted by either deducting the number of basophils counted in step (ii) from the combined total of neutrophils and basophils counted in step (i), or by deducting the number of eosinophils counted in step (i) from the number of leukocytes other than basophils counted in step (ii), in which the information on the size and morphological features of leukocytes in step (i) is determined by irradiating a light to the aliquot of the blood sample treated in step (i) and measuring low and high angle scattered light, said low angle scattered light reflects the size of the leukocytes and the high angle scattered light reflects the morphological features of the leukocytes.

22. The method for classifying and counting leukocytes according to claim 21, in which angles for measuring the low angle scattered light and the high angle scattered light range from 1° to 5° and 6° to 20°, respectively.

23. The method for classifying and counting leukocytes according to claim 6 or 21, in which low and high angle scattered light are measured by using one photodiode (PD) sensor.

* * * * *